United States Patent [19]

O'Brien et al.

[11] Patent Number: 5,030,656
[45] Date of Patent: Jul. 9, 1991

[54] METHODS OF USING COMPOSITIONS COMPRISING (S)-EMOPAMIL FOR USE IN TREATING SPINAL CORD TRAUMA

[75] Inventors: Robert A. O'Brien, Nutley, N.J.; Steven K. Salzman, Wilmington, Del.

[73] Assignee: BASF K&F Corporation, Whippany, N.J.

[21] Appl. No.: 502,350

[22] Filed: Mar. 30, 1990

[51] Int. Cl.$^5$ .......................................... A61K 31/275
[52] U.S. Cl. ..................................... 514/523; 514/929
[58] Field of Search ......................... 514/655, 523, 929

[56] References Cited

U.S. PATENT DOCUMENTS

| | | | |
|---|---|---|---|
| 4,524,072 | 6/1985 | Zivin | 514/280 |
| 4,596,820 | 6/1986 | Raschack et al. | 514/523 |
| 4,898,869 | 2/1990 | Zivin | 514/280 |
| 4,914,125 | 4/1990 | Baldinger et al. | 514/520 |

OTHER PUBLICATIONS

Bieignberg, G. W. et al., J. Cerebral Blood Flow & Metabolism 7:480-488 (1987).
Senter, H. J. et al., J. Neurosurgery 49:569-578 (1978).
Weber, J. et al., Pharmacology 37:38-49 (1988).
Urbanics, R. et al., Adv. Exp. Med. Biol., 248:479-487 (1989).
Faden, A. I., Pharmacolography W Spinal Cord Injury: A Critical Review of Recent Developments, *Clinical Neuropharmacology*, 10(3):193-204 (1987).

Primary Examiner—Richard L. Raymond
Assistant Examiner—Gary E. Hollinden

[57] ABSTRACT

A method of treating injuries in a patient associated with spinal cord trauma is disclosed. The method comprises administering to the patient a therapeutically effective amount of (S)-emopamil or a physiologically acceptable salt thereof.

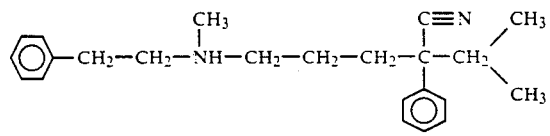

5 Claims, 1 Drawing Sheet

METHODS OF USING COMPOSITIONS COMPRISING (S)-EMOPAMIL FOR USE IN TREATING SPINAL CORD TRAUMA

TECHNICAL FIELD

The field of art to which this invention pertains is pharmaceutical compositions, in particular, the use of these compositions to treat spinal cord trauma.

BACKGROUND OF THE INVENTION

The study of the acute pharmacology of experimental spinal cord injury has been advanced by the discovery of a number of seemingly unrelated therapeutic substances. Thus, opioid antagonists, TRH analogs, antioxidants and excitatory amino acid antagonists have been identified as potential treatments of acute injury. Results obtained using calcium channel blockers have been equivocal, however, none have been developed for this indication. Serotonin antagonists have not been studied in traumas, but have shown positive results in ischemic models of injury.

Serotonin (5-Hydroxy Tryptamine, 5-HT) has been identified to be an important component of secondary spinal trauma. Serotonin appears to form a vital link between the vascular and neural consequences of injury. Positive results have already been obtained using several $5HT_2$ antagonists, including (S)-emopamil.

What is needed in this art are new approaches to treating spinal cord trauma. The combination of calcium channel blocking with $5HT_2$ antagonist properties constitutes a most promising approach, for the treatment of acute neural injury to the spinal cord of varying etiologies.

DISCLOSURE OF THE INVENTION

A method of treating spinal cord injuries is disclosed. The method comprises administering a therapeutically effective amount of a composition comprising (S)-emopamil, or a physiologically acceptable salt thereof to a patient.

The foregoing and other features and advantages of the present invention will become more apparent from the following description.

BEST MODE FOR CARRYING OUT THE INVENTION

Figure 1:
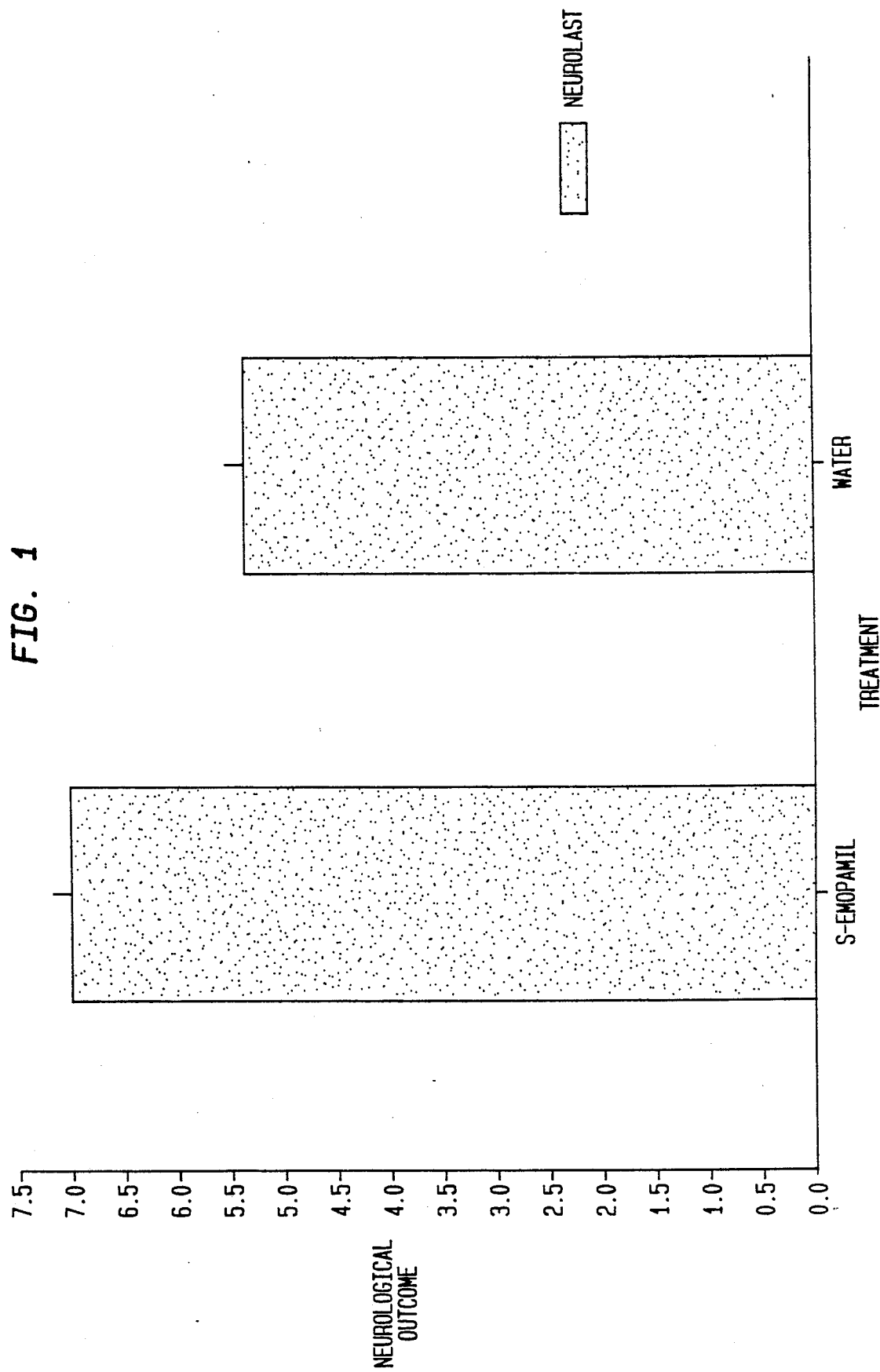
FIG. 1 is a chart illustrating the test results of Example 1.

The pharmaceutical composition (S)-emopamil and the enantiomers and salts thereof are described and disclosed in U.S. Pat. No. 4,596,820 which is incorporated by reference. The compound (S)-emopamil is chemically defined as (-)1,7 Diphenyl-3-methylaza-7-cyano-8-methylnonane. This compound, its enantiomers and salts may be prepared in accordance with the methods and processes disclosed in U.S. Pat. No. 4,596,820. The salts of (S)-emopamil are the salts of suitable physiologically tolerated acids.

(S)-emopamil can be administered in a conventional manner such as orally, parenterally (including, but not limited to, intravenously, intramuscularly, subcutaneously, intrathecally) or rectally.

Examples of suitable physiologically tolerated acids include, but are not limited to, hydrochloric acid, hydrobromic acid, sulfuric acid, phosphoric acid, acetic acid, maleic acid, lactic acid, tartaric acid, citric acid and fumaric acid.

The dosage depends on the age, condition and weight of the patient and on the mode of administration. A sufficient amount of the drug substance is administered to obtain the desired therapeutic effect. As a rule, the typical daily dose of active drug substance is from about 1 to about 50 mg/kg body weight on oral and rectal administration and from about 0.1 to about 5 mg/kg body weight on parenteral administration. A preferred daily dose for oral or rectal administration is about 1 to about 20 mg/kg body weight. A preferred daily dose for parenteral administration is about 0.1 to about 4.0 mg/kg body weight.

(S)-emopamil can be used in conventional solid or liquid pharmaceutical forms for administration, for example as tablets, film-coated tablets, sugar-coated tablets, capsules, powders, granules, suppositoreis or solutions. These are prepared in a conventional manner. The active drug substances can be processed in this connection with the conventional pharmaceutical aids such as tablet binders, fillers, preservatives, tablet disintegrants, flow-regulating agents, plasticizers, wetting agents, dispersants, emulsifiers, suppository bases, solvents, retardants and/or antioxidants (cf. *Remington's Practice of Pharmacy*). The forms for administration obtained in this way typically will contain the active substance in an amount of from 1 to 99 percent by weight.

It is surprising and unexpected that treating spinal cord trauma with (S)-emopamil results in significant enhancement of neurological outcome.

The following examples are illustrative of the principles and practices of this invention, although not limited thereto. Parts and percentages where used are parts and percentages by weight.

EXAMPLE 1

Materials and Methods

Male Sprague-Dawley rats (Charles River Laboratory) each weighing between 250–350 g were the subjects of study. Each was housed under identical light-dark conditions for a minimum of two days prior to experimentation to allow for habituation to the animal colony and initial evaluation. The animals were anesthetized with sodium pentobarbital (62 mg/kg, i.p.). Oxygen was delivered through a tight-fitting mask at 2 l/min. Body temperature was maintained between 37°–38° C. using a water-heated pad. A lateral tail vein was catheterized percutaneously using a 24 gauge intravenous catheter (Becton-Dickinson Labs) for drug administration. The animal was then placed in a stereotaxic frame (David Kopf Instruments) with fixation at the external auditory meatuses. A laminectomy was performed via a midline incision, exposing the cord at T10 without disturbing the dura. The skull was exposed and screw electrodes implanted at the nasal sinus and at the intersection of the midline with the bregmoid and lambdoid sutures for the recording of somatosensory-evoked potentials (SSEP) to hindlimb stimulation of the plantar nerve. A minimum of five SSEP recordings, each averaged from 256 stimuli (10–15 volts, 0.5 msec, 3 Hz), were obtained prior to injury. Only animals with consistently reproducible negative responses (i.e. >1 microvolts in amplitude, latency between 12 and 30 msec with a maximum variation of 2 msec within animals) were included in this study.

Following the demonstration of stable SSEP recordings, the animals were prepared for injury by placing additional fixation of the spinous process of T11. A nylon impounder (2 mm diameter at the bottom of a hollow steel tube) was stereotactically lowered onto the exposed dural surface at T10 until its contact with the dorsum of the cord caused exactly 1 mm of movement of the impounder up into the stainless steel cylinder. The impounder was free to move vertically within the cylinder attached to a stereotaxic micromanipulator allowing uniform tension to be applied to the cord in all animals. With the dura intact, the spinal cord was injured at T10 using a weight-drop method. In this method, a weight (10 gm) is dropped a fixed distance (5 cm) through the cylinder onto the nylon impounder striking the exposed dura (i.e. 50 g cm injury). This 50 g cm injury causes a moderate, reproducible, but incomplete spinal injury with ca 70% of vehicle-treated animals showing a loss of locomotor function at two weeks.

Somatosensory-evoked potentials were recorded immediately after injury and at 5, 10, and 15 minutes post-injury. Animals were excluded from the study whose SSEP returned within this time period. Following this 15 minute post-injury period, all animals were randomly and blindly assigned to a treatment or vehicle group. All drugs were dissolved in sterile water and passed through a 0.22 micron micropore filter (Gelman) prior to their intravenous administration. The drug injections were preceded and followed by the i.v. administration of 0.3 ml of sterile saline. Following the injections, SSEP's were recorded at 20, 25, and 30 minutes post-injury (i.e. 5, 10, and 15 minutes post-injection), after which the animals wounds were closed in layers, the monitoring devices removed and the animals returned to their cages for a two-week period of post-operative neurologic evaluation. Only those animals surviving the full two-week post-operative period were included in the anlysis.

Neurologic Assessment

Post-operatively, behavioral neurologic function was evaluated by investigators unaware of the animals injury status or drug treatment. Each day, for a period of two weeks, neurologic testing was performed according to a modified Tarlov scale. Each hindlimb was rated as follows:
 0 = total paralysis
 1 = no spontaneous movement by responds to noxious stimulus
 2 = spontaneous movement but cannot stand
 3 = able to support weight but cannot walk
 4 = able to walk with or without spasticity or ataxia
 5 = able to balance on a 1 cm ledge, but not walk on the ledge
 6 = able to walk on 1 cm ledge - normal function Post-operative survival was determined in all animals surviving greater than 24 hours after surgery. Final and cumulative neurologic scores were compared only in animals surviving the full 2-week period. Walking ability was assessed, being defined as a neurologic score of 4 or greater in both hindlimbs. Finally, hindlimb strength was determined using the Rivlin-Tator angle board test prior to sacrifice. The maximum angle of incline maintained for 5 sec in the horizontal plane was measured. Test results are illustrated in FIG. 1. FIG. 1 demonstrates that animals treated with (S)-emopamil as compared to vehicle exhibited a greater composite neurological rating, indicating better neurological outcome. Dosing regimen for the preliminary findings described above and in FIG. 1 was 1 mg/kg of (S)-emopamil administered 15 minutes post injury. After the 2-week post-operative survival period, all animals were sacrificed and their spinal cords were removed for biochemical analysis.

Measurement of Spinal Indoleamines

The spinal cord of each animal surviving the 2-week period was harvested and sectioned into three 5 mm segments: I - centered at the injury site; P - proximal to the injury; D - distal to the injury. The proximal and distal segments were weighed and stored at −70° C. Spinal cord concentrations of serotonin (5-HT) and 5-hydroxyindole acetic acid (5-HIAA) are determined by liquid chromatography with dual electrochemical detection, as documented and described extensively in previous work. These data are used as an index of long-tract axon survival by determining the functional state of axoplasmic transport of 5-HT and 5-HIAA through the lesion site. Specifically, a depletion of indoles below the site of injury (D) and their accumulation proximally (P), is interpreted as a result of restricted or blocked transport mechanisms in physically or functionally transacted fibers. The ratio of indole concentrations in segment D over segment P are compared between treatment groups. The injured segment is stored in 10% unbuffered formalin for histological analysis using a hematoxylin/cosin stain to quantify the injury size and luxol blue stain to quantify the remaining myelinated axons.

EXAMPLE 2

Tablets having the following composition are prepared in a conventional manner on a conventional tableting machine:
 40 mg of the substance (S)-emopamil hydrochloride,
 120 mg of corn starch,
 13.5 mg of gelatine,
 45 mg of lactose,
 2.25 mg of Aerosil R (chemically pure silica in submicroscopically fine dispersion), and
 6.75 mg of potato starch (as a 6% strength paste).

EXAMPLE 3

Coated tablets having the following composition are prepared in a conventional manner:
 20 mg of the substance (S)-emopamil.
 60 mg of core material, and
 60 mg of sugar-coating material.

The core material consists of 9 parts of corn starch, 3 parts of lactose and 1 part of Luviskol R VA64 (60-40 vinylpyrrolidone/vinyl acetate copolymer, cf. *Phar. Ind.* 1962, 586). The sugar-coating material consists of 5 parts of sucrose, 2 parts of corn starch, 2 parts of calcium carbonate and 1 part of talc. The coated tablets prepared in this manner are then provided with a conventional coating resistant to gastric juices.

EXAMPLE 4

10 g of the substances (S)-emopamil and (S)-emopamil hydrochloride are each dissolved in 5,000 ml of water with the addition of NaCL to form separate solutions, and each solution is brought to pH 6.0 with 0.1N NaOH so that a blood-isotonic solution results. 5 ml portions of each solution are introduced into ampoules and sterilized.

Although this invention has been shown and described with respect to the detailed embodiments thereof, it will be understood by those skilled in the art that various changes in form and detail thereof may be made without departing from the spirit and scope of the claimed invention.

I claim:

1. A method for treating spinal cord trauma in a patient which comprises administering to said patient a therapeutically effective amount of a composition comprising (S)-emopamil or a physiologically acceptable salt thereof in combination with a pharmaceutically acceptable carrier.

2. The method of claim 1, wherein said composition comprises a physiologically acceptable salt of (S)-emopamil.

3. The method of claim 2, wherein said salt comprises (S)-emopamil hydrochloride.

4. The method of claim 1, wherein said composition is administered orally.

5. The method of claim 1, wherein said composition is administered parenterally.

* * * * *